(12) United States Patent
Foster et al.

(10) Patent No.: US 9,026,213 B2
(45) Date of Patent: May 5, 2015

(54) MEDICAL DEVICE LEAD WITH CONDUCTOR FRACTURE PREDICTION

(75) Inventors: Arthur J. Foster, Centerville, MN (US); Christopher Perrey, Victoria, MN (US); Jeffrey E. Stahmann, Ramsey, MN (US); Scott R. Stubbs, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 191 days.

(21) Appl. No.: 13/548,943

(22) Filed: Jul. 13, 2012

(65) Prior Publication Data

US 2013/0041444 A1    Feb. 14, 2013

Related U.S. Application Data

(60) Provisional application No. 61/522,774, filed on Aug. 12, 2011.

(51) Int. Cl.
| | | |
|---|---|---|
| *A61N 1/375* | (2006.01) | |
| *A61N 1/04* | (2006.01) | |
| *A61N 1/37* | (2006.01) | |
| *A61N 1/08* | (2006.01) | |

(52) U.S. Cl.
CPC ............. *A61N 1/375* (2013.01); *A61N 1/0488* (2013.01); *A61N 1/3752* (2013.01); *A61N 1/048* (2013.01); *A61N 1/37* (2013.01); *A61N 2001/083* (2013.01)

(58) Field of Classification Search
CPC ... A61N 1/0472; A61N 1/048; A61N 1/0488; A61N 2001/083; A61N 2001/37241; A61N 2001/375; A61N 2001/3752; A61N 2001/37294

USPC ............ 607/27, 28, 36, 37, 62, 63, 115, 116; 600/372

See application file for complete search history.

(56) References Cited

U.S. PATENT DOCUMENTS

| | | | | |
|---|---|---|---|---|
| 4,033,355 A | * | 7/1977 | Amundson | .................... 607/122 |
| 5,366,493 A | * | 11/1994 | Scheiner et al. | .............. 607/116 |
| 5,558,098 A | | 9/1996 | Fain | |

(Continued)

FOREIGN PATENT DOCUMENTS

| | | |
|---|---|---|
| JP | 2001245991 A | 9/2001 |
| JP | 2008520374 A | 6/2008 |

(Continued)

OTHER PUBLICATIONS

International Search Report and Written Opinion issued in PCT/US2012/046714, mailed Oct. 5, 2012.

(Continued)

*Primary Examiner* — Carl H Layno
*Assistant Examiner* — Eugene Wu
(74) *Attorney, Agent, or Firm* — Faegre Baker Daniels LLP

(57) ABSTRACT

A medical device lead includes a lead body having a proximal end and a distal end. The proximal end is configured for connection to a pulse generator. One or more electrodes are at a distal end of the lead body, and a lead conductor extends through the lead body and is electrically coupled to at least one of the one or more electrodes. The conductor is configured to deliver electrical signals between the proximal end and the at least one of the one or more electrodes. A sacrificial conductor extends through the lead body adjacent to lead conductor and is configured to fail at a lower stress than the lead conductor.

6 Claims, 3 Drawing Sheets

(56) References Cited

U.S. PATENT DOCUMENTS

| | | | |
|---|---|---|---|
| 5,954,759 A * | 9/1999 | Swoyer et al. | 607/122 |
| 6,061,598 A | 5/2000 | Verness et al. | |
| 6,285,910 B1 | 9/2001 | Verness et al. | |
| 6,295,476 B1 | 9/2001 | Schaenzer | |
| 6,720,497 B1 * | 4/2004 | Barsne | 174/102 R |
| 6,950,710 B2 * | 9/2005 | Shirakawa et al. | 607/122 |
| 7,065,411 B2 * | 6/2006 | Verness | 607/116 |
| 7,486,994 B2 * | 2/2009 | Zarembo et al. | 607/116 |
| 7,519,432 B2 * | 4/2009 | Bolea et al. | 607/116 |
| 7,660,635 B1 | 2/2010 | Verness et al. | |
| 8,108,053 B2 | 1/2012 | Zhao | |
| 8,639,352 B2 * | 1/2014 | Wang et al. | 607/116 |
| 2002/0099430 A1 * | 7/2002 | Verness | 607/122 |
| 2004/0064161 A1 * | 4/2004 | Gunderson et al. | 607/28 |
| 2004/0215300 A1 * | 10/2004 | Verness | 607/116 |
| 2006/0111632 A1 | 5/2006 | Chen | |
| 2010/0174349 A1 | 7/2010 | Stevenson et al. | |
| 2010/0204767 A1 | 8/2010 | Zhao | |

FOREIGN PATENT DOCUMENTS

| | | |
|---|---|---|
| JP | 2011512199 A | 4/2011 |
| JP | 2012055480 A | 3/2012 |

OTHER PUBLICATIONS

International Preliminary Report on Patentability, Chapter II, issued in PCT/US2012/046714, mailed Nov. 27, 2013, 6 pages.

* cited by examiner

MEDICAL DEVICE LEAD WITH CONDUCTOR FRACTURE PREDICTION

CROSS-REFERENCE TO RELATED APPLICATION

This application claims priority to Provisional Patent Application No. 61/522,774, filed Aug. 12, 2011, which is herein incorporated by reference in its entirety.

TECHNICAL FIELD

The present invention relates to implantable medical devices. More specifically, the present invention relates to a medical device lead including a sacrificial conductor for predicting fracture of lead conductors.

BACKGROUND

During normal daily activity of a patient, medical device leads flex through a large number of cycles and withstand various other stresses. Numerous cycles of flexing causes fatigue damage and failure in leads, and other stresses such as axial stress can further cause lead damage. Leads are particularly susceptible to fatigue damage or failure at stress concentration points along the lead. Examples of stress concentration points include, but are not limited to where a lead exits a pulse generator, or where a lead is attached to a more rigid structure such as an electrode. Kinking in a flexural direction and crushing in a radial direction may also be problems in stress concentration points.

Leads may follow narrow and tortuous paths which may require short electrodes to navigate tight bends, thus creating more stress concentration points. Additionally, the designed size of leads is decreasing with industry pressure to make less invasive products. Smaller leads tend to be more fragile, which further increases the need for more robust lead designs that can withstand numerous flex cycles and axial stresses.

SUMMARY

Discussed herein are various embodiments of sacrificial conductors configured for fracture prediction in implantable medical electrical leads, as well as medical electrical leads including the sacrificial conductors.

In Example 1, a medical device lead includes a lead body having a proximal end and a distal end. The proximal end is configured for connection to a pulse generator. One or more electrodes are at a distal end of the lead body, and a lead conductor extends through the lead body and is electrically coupled to at least one of the one or more electrodes. The conductor is configured to deliver electrical signals between the proximal end and the at least one of the one or more electrodes. A sacrificial conductor extends through the lead body adjacent to lead conductor and is configured to fail at a lower stress than the lead conductor.

In Example 2, the medical device lead according to Example 1, wherein the lead conductor comprises a conductive coil, and wherein the sacrificial conductor is coaxial with the lead conductor.

In Example 3, the medical device lead according to either Example 1 or 2, wherein the sacrificial conductor comprises at least one filar disposed between filars of the conductive coil.

In Example 4, the medical device lead according to any of Examples 1-3, wherein the sacrificial conductor is coupled to at least one of the one or more electrodes.

In Example 5, the medical device lead according to any of Examples 1-4, wherein the sacrificial conductor extends from the proximal end of the lead body, to the distal end of the lead body, and back to the proximal end of the lead body.

In Example 6, the medical device lead according to any of Examples 1-5, wherein the sacrificial conductor comprises a filar having an inner conductive layer and an outer conductive layer, wherein the inner conductive layer has a different tensile strength than the outer conductive layer.

In Example 7, a medical device includes a pulse generator and a lead. The lead includes a connector configured to couple with the pulse generator, a lead body including a proximal end and a distal end, and one or more electrodes. A lead conductor extends through the lead body and is electrically coupled between the connector and at least one of the one or more electrodes. The conductor is configured to deliver electrical signals between the pulse generator and the at least one of the one or more electrodes. A sacrificial conductor extends through the lead body adjacent to lead conductor. The sacrificial conductor is electrically coupled to the connector and is configured to fail at a lower stress than the lead conductor.

In Example 8, the medical device according to Example 7, wherein the pulse generator is configured to periodically measure an electrical property of the sacrificial conductor, and wherein a measured change in the electrical property of the sacrificial conductor indicates a failure in the sacrificial conductor.

In Example 9, the medical device according to either Example 7 or 8, wherein the lead conductor comprises a conductive coil, and wherein the sacrificial conductor is coaxial with the lead conductor.

In Example 10, the medical device according to any of Examples 7-9, wherein the sacrificial conductor comprises at least one filar disposed between filars of the conductive coil.

In Example 11, the medical device according to any of Examples 7-10, wherein the sacrificial conductor is coupled to the at least one of the one or more electrodes.

In Example 12, the medical device according to any of Examples 7-11, wherein the sacrificial conductor extends from the proximal end of the lead body, to the distal end of the lead body, and back to the proximal end of the lead body.

In Example 13, the medical device according to any of Examples 7-12, wherein the sacrificial conductor comprises a filar having an inner conductive layer and an outer conductive layer, and wherein the inner conductive layer has a different tensile strength than the outer conductive layer.

In Example 14, a medical device lead comprises one or more electrodes, a lead conductor electrically coupled to at least one of the one or more electrodes, and a sacrificial conductor extending through the lead body adjacent to lead conductor. The lead conductor is configured to deliver electrical signals to at least one of the one or more electrodes. The sacrificial conductor extending through the lead body adjacent to lead conductor, the sacrificial conductor configured to fracture at lower stress than the lead conductor.

In Example 15, the medical device lead according to Example 14, wherein the lead conductor comprises a conductive coil, and wherein the sacrificial conductor is coaxial with the lead conductor.

In Example 16, the medical device lead according to either Example 14 or 15, wherein the sacrificial conductor comprises at least one filar disposed between filars of the conductive coil.

In Example 17, the medical device lead according to any of Examples 14-16, wherein the sacrificial conductor is coupled to at least one of the one or more electrodes.

In Example 18, the medical device lead according to any of Examples 14-17, wherein the sacrificial conductor comprises a filar having an inner conductive layer and an outer conductive layer, wherein the inner conductive layer has a different tensile strength than the outer conductive layer.

In Example 19, the medical device lead according to any of Examples 14-18, wherein the sacrificial conductor extends from a proximal end of the lead, to a distal end of the lead, and back to the proximal end of the lead.

In Example 20, the medical device lead according to any of Examples 14-19, wherein the lead conductor comprises a coating that increases the fatigue resistance of the lead conductor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
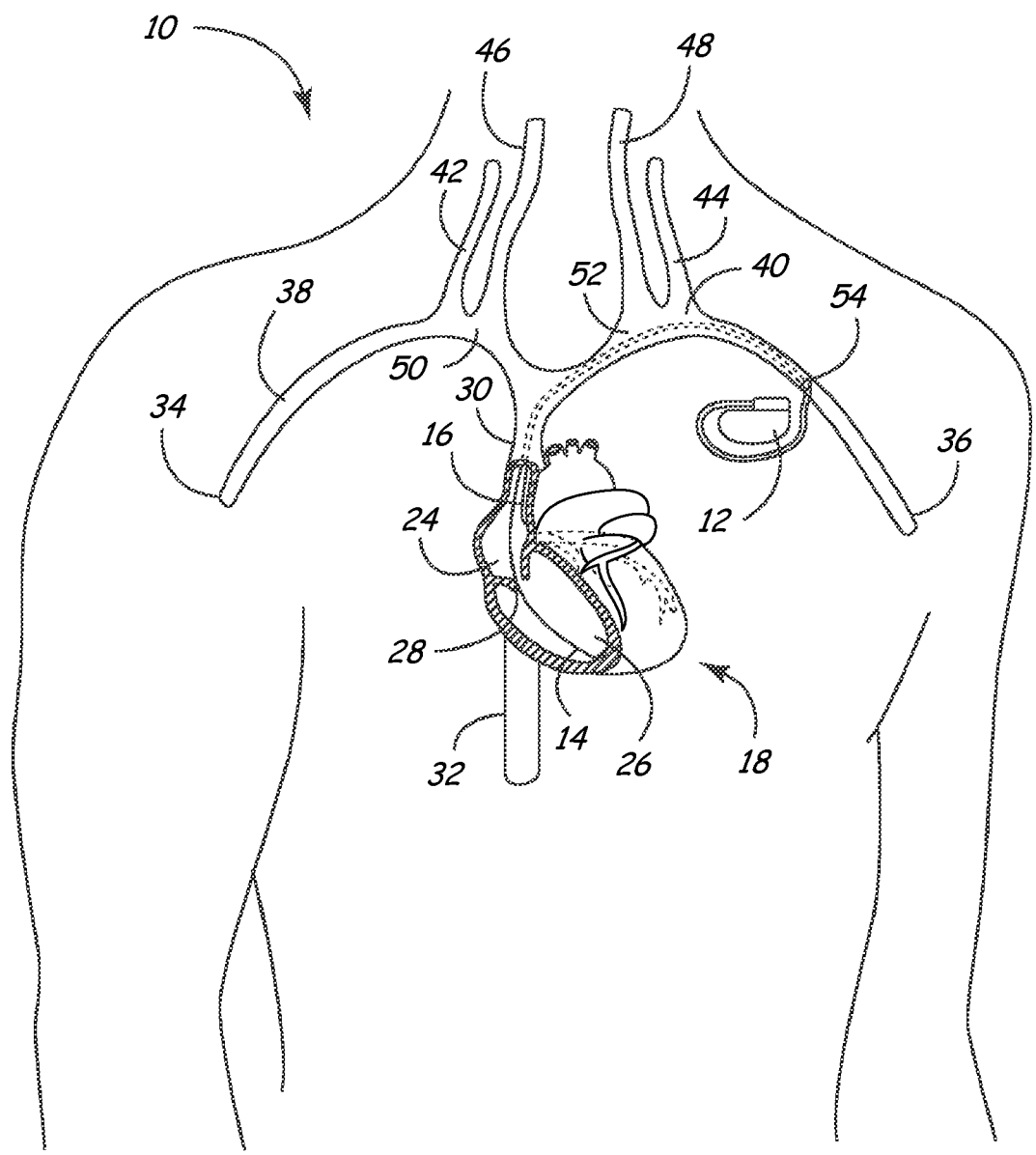
FIG. 1 is a schematic view of a cardiac rhythm management (CRM) system including a pulse generator and a lead implanted in a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments of the present disclosure, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be an implantable medical device known in the art or later developed, for delivering an electrical therapeutic stimulus to the patient. In various embodiments, the pulse generator 12 is a pacemaker, an implantable cardiac defibrillator, and/or includes both stimulation and defibrillation capabilities. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired endocardial or epicardial implantation site, is generally coiled up in the subcutaneous pocket near the pulse generator 12.

The electrical signals and stimuli conveyed by the pulse generator 12 are carried to electrodes at the distal ends of leads 14, 16 by one or more conductors extending through the leads 14, 16. The one or more conductors are each electrically coupled to a connector suitable for interfacing with the pulse generator 12 at the proximal end of the leads 14, 16 and to one or more electrodes at the distal end.

After implantation, the leads 14, 16 are subject to repeated forces that exert stress on components of the leads 14, 16, including the lead conductors that deliver signals to the electrodes. These forces may be caused by involuntary and voluntary movements of the patient's anatomy surrounding the leads 14, 16. The stresses on the lead conductors can have an effect on the performance of the leads 14, 16 over time. According to embodiments of the CRM system 10 disclosed herein, the leads 14 and/or 16 may include features that predict loss of integrity of the lead conductor before performance of the leads 14, 16 is affected. In particular, the leads 14 and/or 16 may include a sacrificial conductor adjacent to the lead conductor(s) that fracture or otherwise fail at a lower stress than the lead conductors. For example, the sacrificial conductor may have a lower tensile strength than the lead conductor(s), and/or the sacrificial conductor may include intentionally induced stress points. When the sacrificial conductor fails, a change in an electrical property (e.g., impedance, inductance, capacitance, signal propagation time) in the sacrificial conductor may be measured by the pulse generator 12. When the pulse generator 12 detects failure of the sacrificial conductor, steps may be taken to replace or repair the lead(s) 14, 16 in which the sacrificial conductor failed or to reconfigure the implanted system to minimize effects of predicted lead conductor failure on the patient.

Figure 2:
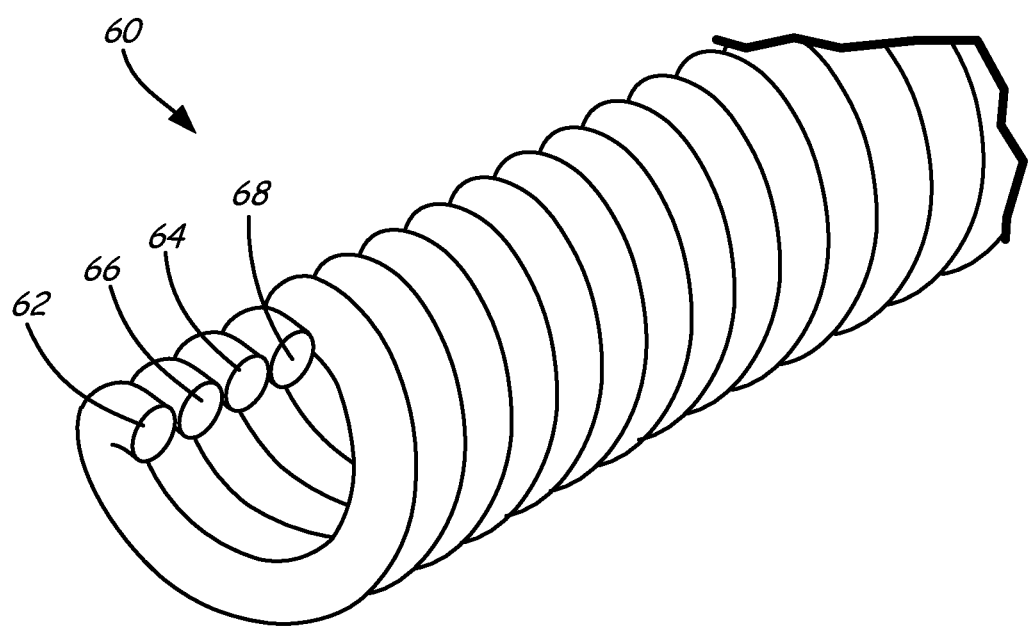
FIG. 2 is a perspective view of a portion of a lead conductor and a co-radial sacrificial conductor.

FIG. 2 is a perspective view of a portion of a conductor assembly 60 including an embodiment of a fracture prediction feature. The conductor assembly 60 includes lead conductors 62 and 64, and sacrificial conductors 66, 68. The lead conductors 62, 64 are co-radial with the sacrificial conductors 66, 68. Turns of the sacrificial conductors 66, 68 are disposed between turns of the lead conductors 62, 64. In the embodiment shown, the lead conductors 62, 64 and sacrificial conductors 66, 68 each comprises a single filar. In alternative embodiments, the lead conductors 62, 64 and/or sacrificial conductors 66, 68 comprises two or more filars. The conductor assembly 60 may alternatively include a single lead conductor and/or a single sacrificial conductor. In addition, the lead conductors 62 and/or 64 may alternatively have other forms, such as a cable conductor. In some embodiments, the pitch, filar diameter, and outer diameter of the lead conductors 62, 64 and sacrificial conductors 66, 68 are controlled to minimize effects of magnetic resonance imaging (MRI) fields on the performance of the lead 14.

The lead conductors 62, 64 and sacrificial conductors 66, 68 extend through the body of the lead 14. While the following discussion describes embodiments with respect to the lead 14, the embodiments are also applicable to the lead 16. In some embodiments, the lead conductors 62, 64 and sacrificial conductors 66, 68 are coupled to a connector at the proximal end of the lead 14. The connector is configured to electrically couple the lead conductors 62, 64 and sacrificial conductors 66, 68 to the pulse generator 12. The lead conductors 62, 64 are coupled to one or more electrodes at a distal end of the lead 14 such that electrical signals may be communicated between the pulse generator 12 and one or more electrodes. In some embodiments, the lead conductors 62, 64 are coupled to different electrodes and carry different electrical signals between the pulse generator 12 and the one or more electrodes. The one or more electrodes may include, for example, tip, ring, or helical electrodes, depending on the functions of the lead 14.

The sacrificial conductors 66, 68 may also be connected to one or more electrodes at the distal end of the lead 14. The sacrificial conductors 66, 68 may be connected to the same electrodes as the lead conductors 62, 64, or different electrodes than the lead conductors 62, 64. In one exemplary embodiment, the sacrificial conductors 66, 68 are connected to electrodes on an IS-4 lead that are not used by the lead conductors 62, 64 during lead functions. In alternative embodiments, the sacrificial conductors 66, 68 are not connected to the connector and/or electrodes, and are instead each directly connected to the lead conductors 62, 64. In some embodiments, the sacrificial conductors 66, 68 extend from the proximal end to the distal end of the lead 14. In alternative embodiments, the sacrificial conductors 66 and/or 68 extend through only a portion of the lead 14, such as the portions of the lead 14 at the proximal end subject to the greatest stresses.

The sacrificial conductors 66, 68 are configured to have a lower tensile strength than the lead conductors 62, 64, such that the sacrificial conductors 66, 68 is configured to fracture or otherwise fail at a lower stress than the lead conductors 62, 64. The tensile strength of the sacrificial conductors 66, 68 is such that the sacrificial conductors 66, 68 fail at high stress levels, but a safe margin below the stress levels at which the lead conductors 62, 64 fail. In some embodiments, the sacrificial conductors 66, 68 have a tensile strength that is about 80 percent to about 90 percent the tensile strength of the lead conductors 62, 64. The difference in tensile strength between the lead conductors 62, 64, and the sacrificial conductors 66, 68 can be provided by the material properties and/or geometries of the conductors.

In some embodiments, the lead conductors 62, 64 are comprised of a metal with higher fracture resistance than the metal of the sacrificial conductors 66, 68. In one exemplary implementation, the lead conductors 62, 64 are comprised of MP35N, and the sacrificial conductors 66, 68 are comprised of tantalum. In some embodiments, the sacrificial conductors 66 and/or 68 comprise an inner conductive layer surrounded by an outer conductive layer, where the inner conductive layer has a different tensile strength or fracture resistance than the outer conductive layer. For example, the sacrificial conductors 66 and/or 68 may comprise a metal-to-metal composite. In some embodiments, the sacrificial conductors 66, 68 are configured to have controllably poor surface characteristics designed to fail before the lead conductors 62, 64.

To increase the fatigue resistance of the lead conductors 62, 64 relative to the sacrificial conductors 66, 68, a coating or layer of a polymeric material may additionally or alternatively be formed over the lead conductors 62, 64, while leaving the sacrificial conductors 66, 68 uncoated. In some embodiments, the sacrificial conductors 66, 68 may also be coated with a polymeric material. Example polymeric materials that may be used to coat the lead conductors 62, 64 and/or sacrificial conductors 66, 68 may include, but are not limited to, ETFE, PTFE, and/or polyimide.

When implanted, the pulse generator 12 is configured to take periodic impedance measurements of the sacrificial conductors 66, 68 to determine if the sacrificial conductors 66, 68 have failed. More specifically, the sacrificial conductors 66, 68 may have a known impedance when the lead 14 is implanted. This impedance may be stored in the pulse generator 12. When the impedance of the sacrificial conductors 66, 68 is measured by the pulse generator 12, the pulse generator 12 may compare the measured impedance with the stored impedance of the sacrificial conductors 66, 68. If the measured impedance is outside of an acceptable range with respect to the known impedance, the pulse generator 12 may set a flag or other internal indicator that indicates that the sacrificial conductors 66, 68 has failed. Generally, the impedance of the sacrificial conductors 66, 68 increases upon fracture or failure. Alternatively, the impedance of the sacrificial conductors 66, 68 may be erratic due to intermittent contact of portions of the sacrificial conductors 66, 68 at the point of failure. When the pulse generator 12 connects to an external programmer after impedance measurements indicate a fracture or failure, the flag or indicator is presented to the clinician. The lead 14 may then be replaced or monitored at more frequent intervals to assure that the integrity of the lead conductors 62, 64 remains uncompromised.

The frequency of the impedance measurements (e.g., hourly, daily, weekly, etc.) may be based on power consumption considerations and the risk of failure of the sacrificial conductors 66, 68. For example, early in the life of the lead 14, the impedance measurements may be taken less frequently to conserve the battery life of the pulse generator 12. On the other hand, after the lead 14 has been implanted for a period of time, the impedance measurements may be taken more frequently to ensure failure of the sacrificial conductors 66 or 68 is detected shortly after the failure occurs. The pulse generator 12 may be programmed to automatically adjust the frequency of the impedance measurements over time, or an external programmer may be employed to reprogram the impedance measurement frequency of the pulse generator 12.

Figure 3:
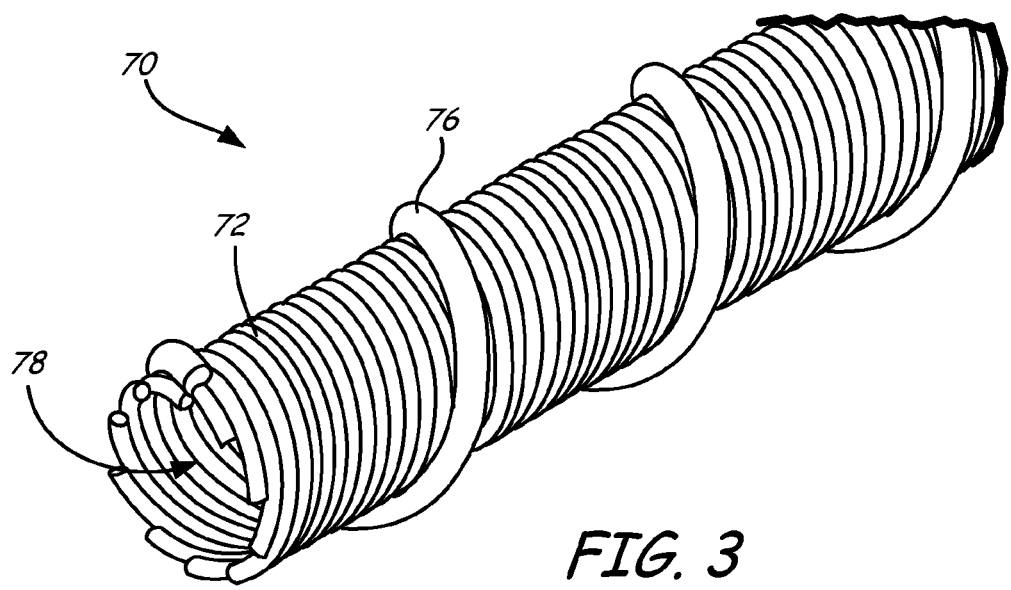
FIG. 3 is a perspective view of a portion of a lead conductor and a co-axial open pitch sacrificial conductor.

FIG. 3 is a perspective view of a portion of a conductor assembly 70 including another embodiment of a fracture prediction feature. The conductor assembly 70 includes lead conductor 72 and sacrificial conductor 76. In the embodiment shown, the lead conductor 72 is configured as a conductive coil. The lead conductor 72 may alternatively have other forms, such as a cable conductor.

The sacrificial conductor 76 is co-axial with the conductive coil of the lead conductor 72. In the embodiment shown, the sacrificial conductor 76 is configured as an open pitch coil formed around an outer diameter of the conductive coil. In alternative embodiments, the sacrificial conductor 76 is configured as a conductive cable including a single filar or a bundle of a plurality of filars, and/or is disposed in the lumen 78 of the lead conductor 72. As with the embodiments described above, the sacrificial conductor 76 is configured to have a lower tensile strength than the lead conductor 72, such that the sacrificial conductor 76 fractures or otherwise fails at a lower stress than the lead conductor 74. The sacrificial conductor 76 may have materials properties and physical characteristics similar to those discussed above with regard to sacrificial conductors 66, 68.

In some embodiments, the lead conductor 72 and sacrificial conductor 76 each comprises a single filar. In alternative embodiments, the lead conductor 72 and/or sacrificial conductor 76 comprise two or more filars. The conductor assembly 70 may alternatively include multiple lead conductors and/or multiple sacrificial conductors. In some embodiments, the pitch, filar diameter, and outer diameter of the lead conductor 72 and sacrificial conductor 76 are controlled to minimize effects of MRI fields on the performance of the lead 14.

The lead conductor 72 and sacrificial conductor 76 extend through the body of the lead 14. In some embodiments, the lead conductor 72 and sacrificial conductor 76 are coupled to a connector at the proximal end of the lead 14. The connector is configured to electrically couple the lead conductor 72 and sacrificial conductor 76 to the pulse generator 12. The lead conductor 72 is coupled to one or more electrodes at a distal end of the lead 14 such that electrical signals may be communicated between the pulse generator 12 and one or more electrodes.

The sacrificial conductor 76 may also be connected to one or more electrodes at the distal end of the lead 14. The sacrificial conductor 76 may be connected to the same electrodes as the lead conductor 72, or different electrodes than the lead conductor 72. In alternative embodiments, the sacrificial conductor 76 is not connected to the connector and/or electrodes. For example, the sacrificial conductor 76 may be connected in parallel to the lead conductor 72. In some embodiments, the sacrificial conductor 76 extends from the proximal end to the distal end of the lead 14. In other embodiments, the sacrificial conductor 76 extends from the proximal end of the lead 14, to the distal end of the lead 14, and back to the proximal end of the lead 14. The sacrificial conductor 76 may be connected to an electrode at the distal end of the lead 14 to provide a resistance path contact for the sacrificial conductor 76. In further embodiments, the sacrificial conductor 76 extends through only a portion of the lead 14, such as the portions of the lead 14 at the proximal end subject to the greatest stresses.

Similar to the conductive assembly 60 described above with regard to FIG. 2, the pulse generator 12 is configured to take periodic impedance measurements of the sacrificial conductor 76 to determine whether the sacrificial conductor 76 has fractured or failed. If the pulse generator 12 detects a sudden step or increase in the impedance compared to previous impedance measurements, or erratic impedance measurements, the pulse generator 12 sets an indicator noting that the sacrificial conductor 76 has fractured or failed.

Figure 4:
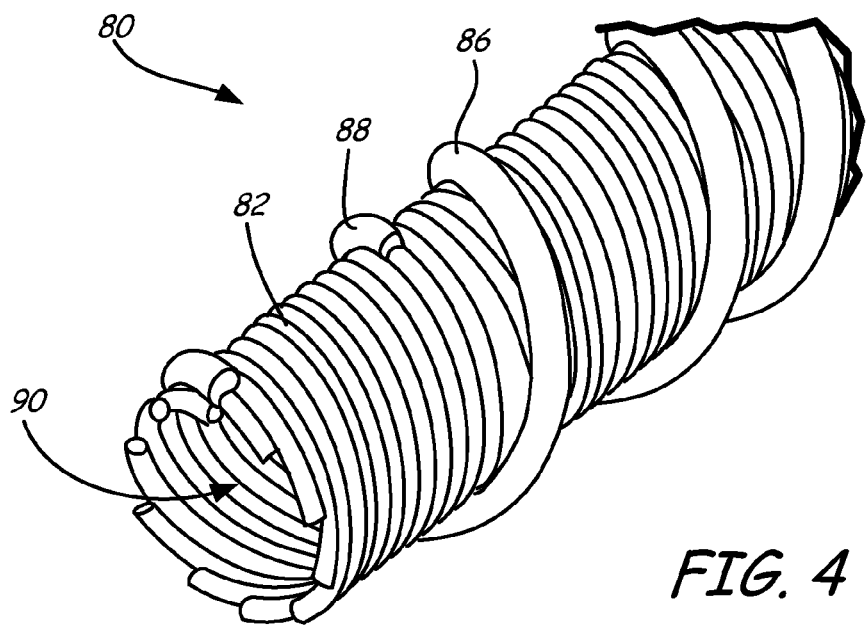
FIG. 4 is a perspective view of a portion of a lead conductor and a plurality of open pitch sacrificial conductors co-axial with the lead conductor and coupled together at a distal end.

FIG. 4 is a perspective view of a portion of a conductor assembly 80 including another embodiment of a fracture prediction feature. The conductor assembly 80 shown in FIG. 4 is a variation of the conductor assembly 70 shown in FIG. 3. The conductor assembly 80 includes lead conductor 82 and sacrificial conductors 86 and 88. In the embodiment shown, the lead conductor 82 is configured as a conductive coil. The lead conductor 82 may alternatively have other forms, such as a cable conductor.

The sacrificial conductors 86, 88 are co-axial with the conductive coil of the lead conductor 82. The sacrificial conductors 86, 88 are co-radial with respect to each other. In the embodiment shown, the sacrificial conductors 86, 88 are configured as open pitch coils formed around an outer diameter of the conductive coil. In alternative embodiments, the sacrificial conductors 86 and/or 88 are configured as a conductive cable including a single filar or a bundle of a plurality of filars, and/or is disposed in the lumen 90 of the lead conductor 82. As with the embodiments described above, the sacrificial conductors 86, 88 are configured to have a lower tensile strength than the lead conductor 82, such that the sacrificial conductors 86, 88 fracture or otherwise fail at a lower stress than the lead conductor 82. The sacrificial conductors 86, 88 may have material properties and physical characteristics similar to those discussed above with regard to sacrificial conductors 66, 68.

In some embodiments, the sacrificial conductors 86, 88 are electrically coupled to each other at a distal end of the lead 14. In this configuration, the sacrificial conductors 86, 88 form a loop structure that provides an electrical path from the proximal end of the lead 14, to the distal end of the lead 14, and back to the proximal end of the lead 14. When the impedance of the looped sacrificial conductors 86, 88 as measured periodically by the pulse generator 12 increases, the electrical continuity of the looped sacrificial conductors 86, 88 is broken, indicating a fracture or failure of the sacrificial conductors 86, 88. For example, the pulse generator 12 measures an infinite impedance in the sacrificial conductors 86, 88 when a complete fracture occurs.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. For example, while embodiments have been described with regard to a cardiac rhythm management system, the failure prediction features may also be employed in other types of implantable lead systems, such as neural stimulation systems and diagnostic-only systems. Accordingly, the scope of the present invention is intended to embrace all such alternatives, modifications, and variations as fall within the scope of the claims, together with all equivalents thereof.

We claim:

1. A medical device comprising:
    a pulse generator; and
    a lead comprising:
        a connector configured to couple with the pulse generator;
        a lead body including a proximal end and a distal end, the connector coupled to the lead body at the proximal end;
        one or more electrodes located on the distal end of the lead body;
        a lead conductor extending through the lead body and electrically coupled between the connector and at least one of the one or more electrodes, the conductor configured to deliver electrical signals between the pulse generator and the at least one of the one or more electrodes; and
        a sacrificial conductor located within the lead body and extending only along the proximal end of the lead body, the sacrificial conductor located adjacent to the lead conductor, the sacrificial conductor electrically coupled to the connector, the sacrificial conductor configured to fail at a lower stress than the lead conductor.

2. The medical device of claim 1, wherein the lead conductor comprises a conductive coil, and wherein the sacrificial conductor is coaxial with the lead conductor.

3. The medical device of claim 2, wherein the sacrificial conductor comprises at least one filar disposed between filars of the conductive coil.

4. The medical device of claim 1, wherein the pulse generator is configured to periodically measure an impedance of the sacrificial conductor, and wherein a measured increase in the impedance of the sacrificial conductor indicates a failure in the sacrificial conductor.

5. The medical device of claim 1, wherein the pulse generator is configured to periodically measure an electrical characteristic the sacrificial conductor to detect fracture of the sacrificial conductor, the frequency of the measurement increasing over time.

6. The medical device of claim 1, wherein the sacrificial conductor comprises a filar having an inner conductive layer and an outer conductive layer, and wherein the inner conductive layer has a different tensile strength than the outer conductive layer.

* * * * *